United States Patent [19]

Beutler et al.

[11] Patent Number: 5,236,837
[45] Date of Patent: Aug. 17, 1993

[54] ENZYMATIC REAGENT FOR D-MALATE DETERMINATION

[75] Inventors: Hans-Otto Beutler; Gunter Lang, both of Tutzing; Klaus Kaluza, Habach, all of Fed. Rep. of Germany

[73] Assignee: Boehringer Mannheim GmbH, Mannheim, Fed. Rep. of Germany

[21] Appl. No.: 564,521

[22] Filed: Aug. 9, 1990

[30] Foreign Application Priority Data

Aug. 25, 1989 [DE] Fed. Rep. of Germany ....... 3928209

[51] Int. Cl.$^5$ .................................................. C12N 9/04
[52] U.S. Cl. ..................................... 435/190; 435/184; 435/810
[58] Field of Search .................... 435/190, 184, 810

[56] References Cited

U.S. PATENT DOCUMENTS

| | | | |
|---|---|---|---|
| 4,011,169 | 3/1977 | Diehl et al. | 252/95 |
| 4,191,613 | 3/1980 | Ullman et al. | 435/188 |
| 4,543,327 | 9/1985 | Bernstein | 435/26 |
| 4,550,079 | 10/1985 | Röder et al. | 435/189 |
| 4,591,555 | 5/1986 | Bernstein | 435/184 |
| 4,613,569 | 9/1986 | Geisler et al. | 435/810 |
| 4,927,752 | 5/1990 | Remacle | 435/8 |

FOREIGN PATENT DOCUMENTS 0089640 3/1984 European Pat. Off. .

OTHER PUBLICATIONS

Murphey et al., J. Biol. Chem., vol. 242(7), 1967, pp. 1560-1565.

Sanwal et al., J. Biol. Chem., vol. 244(7), 1969, pp. 1817-1823.
McAlister-Henn et al., J. Bact., vol. 169(11)., 1987, pp. 5157-5166.
Murphey et al., J. Biol. Chem., vol. 242(7), 1967, pp. 1548-1559.
Yueh et al., Biochem. J., vol. 258, 1989, pp. 221-228.
Sanwal et al., J. Biol. Chem., vol. 244(7), 1969, pp. 1824-1830.
Nature, Band 212, Nr. 5070, Dec. 31, 1966, Stein et al, pp. 1611-1612 "Inducible D-Malic Enzyme in Escherichia Coli".
Acta Chemica Scandinavica, Band 34, 1980, M. Lähdesmäki et al, "D-Malate Dehydrogenase from Pseudomonas Fluoroescens", pp. 423≧427.
Deutsche Lebensmittel-Rundschau, Band 86, Nov. 11, 1990, H. O. Beutler et al, "A New Method for the Enzymatic Determination of D-Malic Acid in Foodstuffs", pp. 341-344.

Primary Examiner—Ronald W. Griffin
Assistant Examiner—Pamela S. Webber
Attorney, Agent, or Firm—Nikaido, Marmelstein, Murray & Oram

[57] ABSTRACT

The invention concerns a new NAD$^+$-dependent D-malate dehydrogenase (decarboxylating, E.C. 1.1.1.83) from E. coli which consists of two subunits which each have a molecular weight of about 42 kD (SDS gel) and processes for the isolation of this enzyme from E. coli and for its stabilisation. The invention concerns in addition a method for the determination of D-malate with the D-malate dehydrogenase according to the present invention as well as a reagent for determining D-malate.

9 Claims, No Drawings

ENZYMATIC REAGENT FOR D-MALATE DETERMINATION

DESCRIPTION

The NAD-dependent D-malate dehydrogenase (decarboxylating) [E.C. 1.1.1.83] (D-MDH, D-malic enzyme) can be used for the determination of D-malate (D-malic acid) in an aqueous solution. The enzyme catalyzes the following reaction:

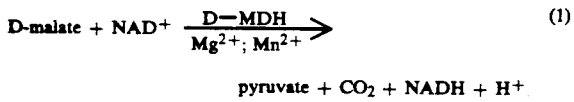

$$\text{D-malate} + \text{NAD}^+ \xrightarrow[\text{Mg}^{2+};\text{Mn}^{2+}]{\text{D-MDH}} \text{pyruvate} + CO_2 + \text{NADH} + H^+ \quad (1)$$

A D-malic enzyme from E. coli K12 (Crookes strain) has been described by Stern and Hegre (Nature 212 (1966), 6111–1612). The enzymatic activity of this D-malic enzyme was only tested in the raw extract. It catalyzes a reaction according to formula (1), i.e. the conversion of D-malate to pyruvate in the presence of NAD+ and $Mg^{2+}$ or $Mn^{2+}$ ions. The presence of $K^+$, $NH_4^+$ or $Rb^+$ ions is necessary for the enzymatic activity. The reaction is inhibited by the addition of EDTA (3.3 μmol/ml). If NADP+ is present in the reaction mixture instead of NAD+, a lower conversion of D-malate to pyruvate and $CO_2$ (8%) is measured in relation to the reaction rate in the presence of NAD+.

A further D-malic enzyme from Pseudomonas fluorescens has been described by Knichel and Radler (Eur. J. Biochem. 123 (1982), 547–552). This D-malic enzyme was purified and stabilized by the addition of 50 mmol/l ammonium sulphate and 1 mmol/l EDTA. An enzyme with a molecular weight of about 175 kD (SDS gel and gel filtration) and a specific activity of 4 to 5 U/mg protein was obtained which was activated by bivalent cations. The activation of the enzymatic activity by manganese ions is not higher than that by magnesium ions. The Km values were 0.3 mmol/l for malate and 0.08 mmol/l for NAD+. The pH optimum for this enzyme is in the range between 8.1 and 8.8.

L-malate is the naturally occurring form of the two stereoisomers of malate. Synthetic malate (consisting of a racemate of D- and L-malate) can be added to fruit juices and wines in order to illegally increase the content of acid. An accurate determination of the D-malate content in the presence of a great excess of L-malate is necessary in order to detect a possible addition of D-malate.

Several methods are already known for measuring the D-malate content. The total amount of malate can thus be measured in fruit juices with a chemical method (Rebelein, Deut. Lebensm. Rundschau 60 (1964) 140–144). The amount of L-malate, which was determined enzymatically, is deducted from this value (Methoden der enzymatischen Analyse, Band 2 (1970), 1544–1548). The difference between both values is the amount of D-malate. This measurement is unreliable because the low D-malate content is derived from the difference between two large numbers. Furthermore, esters and lactones of L-malate cannot be detected using this test procedure.

A second method for the determination of the D-malate content in aqueous solutions is based on the fact that every malic acid produced synthetically (racemate of D- and L-malate) always contains 2 to 5% fumaric acid. Since wine only contains negligibly small amounts of fumaric acid, the detection of fumaric acid using HPLC means that synthetic malic acid i.e. D-malate has also been added to a sample. This test can, however, only be qualitative, since the corresponding fumaric acid content of the racemate of D-malate and L-malate is not known exactly.

The content of D-malate can also be determined using a D-malic enzyme. Thus, Knichel and Radler (Z. Lebensm. Unters. Forsch. 174 (1982) 296–299) have developed a method for the enzymatic determination of D-malate for the D-malic enzyme from Pseudomonas fluorescens. This test has, however, only gained slight importance, because the Pseudomonas enzyme only has a short stability (a few days when stored at 4° C.). Furthermore, the measurement of the D-malate content in fruit juices using the Pseudomonas enzyme is made more difficult by a high proportion of contaminating activities.

It is therefore the object of the present invention to isolate a D-malic enzyme which can be produced in an analytically pure form for use in a D-malate test, which should have a high specificity for D-malate (no interfering contaminating activities), be very stable and which can be used in a D-malate test which can be carried out rapidly and simply.

The invention provides an NAD+-dependent D-malate dehydrogenase (decarboxylating, E.C. 1.1.1.83) from E. coli whose activity does not require the presence of $K^+$, $Rb^+$ or $NH_4^+$ ions.

The activity of this enzyme is not inhibited by EDTA (0.7 mg/ml test solution). In the presence of NADP+ instead of NAD+ the conversion of D-malate to pyruvate and $CO_2$ is less than 0.5% of that in the presence of NAD+. The activity of this enzyme is increased by $Mg^{2+}$ ions but even more by $Mn^{2+}$ ions. The enzyme according to the present invention consists of two subunits which each have a molecular weight of about 42 kD (SDS gel). The Km value for D-malate is 1.1 mmol/l (Tris, pH 8.5 25° C.) or 1.5 mmol/l (HEPES, pH 9.0, 25° C.). The Km value for NAD+ is 0.4 mmol/l (Tris, pH 8.5, 25° C.). The enzyme according to the present invention has a specific activity of at least 25 U/mg protein after purification. It was possible to essentially remove all contaminating activities in the enzyme population by purification: e.g.

| | |
|---|---|
| L-malate dehydrogenase | ≦0.01%, |
| L-lactate dehydrogenase | ≦0.01%, |
| glutamate dehydrogenase | ≦0.01%, |
| β-galactose dehydrogenase | <0.01% and |
| NADH oxidase | <0.01%. |

The invention also includes a process for the isolation of the enzyme by culture of E. coli cells in the presence of malate and isolation of the enzyme from these cells. E. coli DSM 5496 is particularly preferably used. In this process the cells are lysed by conventional means and the raw extract is purified initially by precipitation with polymeric amine (Polymin-G20), acetone precipitation and heating to 56° C. The initially purified enzyme is purified further by anion-exchange (DEAE-Sepharose) chromatography, hydrophobic (phenyl-Sepharose) chromatography, phenyl-Sepharose chromatography, ammonium sulphate precipitation and dialysis.

The invention also provides a process to stabilize an NAD-dependent D-malate dehydrogenase (decarboxylating) in which a copolymer of saccharose and epichlorohydrin (Ficoll), preferably Ficoll 70 (molecular weight 70 kD), is added to a solution of the enzyme which is then lyophilised. In a preferred process the enzyme solution is adjusted to a concentration of 200 U/ml and 30 mg Ficoll 70 per ml enzyme solution is added. The lyophilised enzyme has a residual activity of more than 80% even after five weeks storage at 37° C.

The invention also provides a method for the determination of D-malate in which the enzyme according to the present invention is used. In this process, the conversion of D-malate to pyruvate and $CO_2$ is measured in the presence of $NAD^+$ which is reduced to NADH and $H^+$. A method is preferred in which the formation of NADH is measured photometrically. A method is particularly preferred in which the enzymatic conversion of D-malate is coupled with a colour reaction with tetrazolium salts to increase the sensitivity of the measurement. Using the D-malic enzyme according to the present invention it is possible to determine D-malate concentrations in fruit juices and wine even in the presence of a ca. 250-fold excess of L-malate. The presence of food additives interferes only to a negligible extent with the method according to the present invention.

The common conventional buffer substances such as e.g. Tris, HEPES, glycine, DEA and TES can be used as the buffer substances in a method according to the present invention for the determination of D-malate. Tris or/and HEPES are particularly preferred. The measurement can be carried out in a pH range from 7.5 to 10.0. In this connection, the pH range from 8.0 to 9.5 is preferred and the pH range from 8.8 to 9.1 is preferred most.

The method according to the present invention is carried out at a buffer concentration in the test solution of 20 mmol/l to 200 mmol/l. In this connection, a buffer concentration of 40 mmol/l to 100 mmol/l is preferred and even more preferred is a buffer concentration of the test solution of 50 mmol/l.

The method according to the present invention for the determination of D-malate can be carried out in the presence of $Mg^{2+}$ or $Mn^{2+}$ ions. Although $Mn^{2+}$ ions activate the reaction more strongly, the use of $Mg^{2+}$ ions is preferred since the formation of manganese dioxide ($MnO_2$) can be easily observed in the presence of $Mn^{2+}$. A concentration of $Mg^{2+}$ ions in the test solution of 0.6 mmol/l to 10 mmol/l is suitable. A concentration of $Mg^{2+}$ ions of 1.0 mmol/l to 4.0 mmol/l is preferred, and a concentration of 3.3 mmol/l $Mg^{2+}$ ions in the test solution is preferred most.

The method according to the present invention for the determination of D-malate is carried out at a $NAD^+$ concentration of 0.3 mmol/l to 5.0 mmol/l, preferably 0.6 mmol/l in the test solution.

Finally the invention also provides a reagent for the determination of D-malate which contains the D-MDH, buffer, $Mg^{2+}$ ions and $NAD^+$ according to the present invention. A reagent is preferred which contains Tris and/or HEPES buffer. A reagent is particularly preferred which contains 20 mmol/l to 200 mmol/l Tris or/and HEPES buffer, pH 7.5 to 10, 0.6 mmol/l to 10 mmol/l $Mg^{2+}$ ions and 0.3 mmol/l to 5.0 mmol/l $NAD^+$. A reagent is preferred most which contains 50 mmol/l Tris or/and HEPES buffer, 3.3 mmol/l $Mg^{2+}$ ions and 0.6 mmol/l $NAD^+$.

The following examples should elucidate the invention further.

EXAMPLE 1

1. Fermentation, Concentration and Stabilization of D-MDH

Fermentation

Initial cultures of the *E. coli* strain DSM 5496 are cultured in LB medium (10 g tryptone, 5 g yeast extract, 5 g NaCl per 1000 ml water, pH 7.0 to 7.2).

The following medium is used in the induction of the D-MDH activity:
7.1 g $Na_2HPO_4$,
20 g $K_2HPO_4 \times 3\ H_2O$,
0.25 g $MgSO_4 \times 7\ H_2O$,
2 g $(NH_4)_2SO_4$,
14 mg $CaCl_2 \times 2\ H_2O$,
4 g D,L-malate
per 1000 ml $H_2O$, pH 6.8 to 7.0.

After sterilization the following supplements are added to the medium:

| Vitamins: | |
|---|---|
| thiamine HCl | 1 mg/l |
| p-aminobenzoic acid | 0.2 mg/l |
| pyridoxine | 0.2 mg/l |
| riboflavin | 0.2 mg/l |
| Ca pantothenate | 1 mg/l |
| folic acid | 0.2 mg/l |
| biotin | 1 mg/l |
| Trace elements: | |
| $MgCl_2 \times 4\ H_2O$ | 0.5 mg/l |
| $ZnSO_4 \times 7\ H_2O$ | 1 mg/l |
| $CuSO_4 \times 5\ H_2O$ | 0.5 mg/l |
| $CoCl_2 \times 6\ H_2O$ | 0.5 mg/l |
| $NiCl_2 \times 6\ H_2O$ | 0.5 mg/l |
| $Na_2MoO_4 \times 2\ H_2O$ | 0.05 mg/l |
| $FeCl_3 \times 6\ H_2O$ | 1.5 mg/l |

The cultures are cultured at 37° C. while aerating strongly. The cells are harvested in the late logarithmic growth phase.

Concentration

Lysis:
Suspend 700 g fresh or frozen *E. coli* DSM 5496 cells in 4 volumes cold 50 μmol/l Tris-HCl buffer, pH 7.5. Take 10 ml as an initial sample to determine the enzyme activity. Lyse the bacterial suspension twice using Manton-Gaulin high pressure dispersion at 600 bar. Rinse with cold de-ionised water.
Volume (V): 3.5 l
Total activity: $4.5 \times 10^4$ U.

Polymin G-20 separation

After taking an initial sample, add 1 to 3% of a 10% Polymin G-20 solution, pH 7.0 to the raw extract and centrifuge for 30 minutes on a Beckmann centrifuge.
V=3.5 l
Total activity: $4.5 \times 10^4$ U.

Acetone Precipitation

Add 0.8 volumes deep-cooled acetone to the clear Polymin supernatant and centrifuge for 15 minutes on the Beckmann centrifuge. Take up the acetone precipitate in 1 l Tris-HCl buffer, 50 μmol/l, pH 7.5. Stir for ca. one hour in an ice bath, then centrifuge for 20 minutes on the Beckmann centrifuge.
V=1 l
Total activity: $4 \times 10^4$ U.

Heating

After taking an initial sample (15 minutes, 20 minutes and 25 minutes), the main amount of the resuspended acetone precipitate is heated in a water bath to 56° C. The content of L-malate dehydrogenase should be <1%, the content of glutamate dehydrogenase should be <0.01%. After heating, cool, centrifuge in a Beckmann centrifuge for 20 minutes and filter through glass wool.

V=1 l
Total activity: $3 \times 10^4$ U.

DEAE-Sepharose ff Chromatography

Apply the enzyme solution to a DEAE-Sepharose ff-column equilibrated with 50 μmol/l Tris buffer, pH 8.0.

Capacity: 200 to 250 U/g exchanger
Column dimension: $3 \times 20$ cm (ca. 130 g)
Washing: 10 column volumes Tris buffer 50 μmol/l, pH 8.0; 0.11 mol/l NaCl
Elution: 10 column volumes Tris buffer 50 μmol/l, pH 8.0, 0.18 mol/l NaCl.
Pool all active fractions.
V=250 ml
Total activity = $2.1 \times 10^4$ U.

The content of glutamate dehydrogenase is less than 0.01%, the content of L-malate dehydrogenase is less than 0.01% of the total activity.

Phenyl-Sepharose ff Chromatography

Adjust the pooled active DEAE-Sepharose fractions to a concentration of 1.0 mol/l ammonium sulphate with solid ammonium sulphate. Apply the enzyme solution to a phenyl-Sepharose ff-column equilibrated with Tris buffer 50 μmol/l, pH 7.5 and 1.0 mol/l ammonium sulphate.

Capacity: ca. 200 U/g exchanger
Column dimension: $3 \times 20$ cm (ca. 100 g)
Washing: 10 column volumes Tris buffer 50 μmol/l, pH 7.5; 0.6 mol/l ammonium sulphate.
Elution: 10 column volumes Tris buffer 50 μmol/l, pH 7.5; 0.3 mol/l ammonium sulphate.
Pool all active fractions.
V=300 ml,
Total activity = $1.5 \times 10^4$ U.

The content of lactate dehydrogenase is less than 0.01% of the total activity.

Ammonium Sulphate Precipitation, Dialysis

Adjust pooled eluates to a concentration of 2.5 mol/l ammonium sulphate by addition of ammonium sulphate. Centrifuge for 30 minutes in the Beckmann centrifuge and take up the precipitate in a concentrated form in 50 μmol/l Tris buffer, pH 7.5 and dialyse exhaustively against this buffer overnight at 4° C.

V=75 ml,
Total activity = $1.2 \times 10^4$ U.

Lyophilisation

Adjust the dialysate to a concentration of 200 U D-MDH/ml with dialysis buffer and add 30 ml Ficoll 70 (polymeric saccharose, cross-linked with epichlorohydrin MW=70000), which was predissolved in $H_2O$, per ml enzyme solution and lyophilise. Yield: 10000 U D-MDH Specific activity: 25 U/ml protein Total amount of lyophilisate: 2.3 g. 100 mg lyophilisate contains 67 mg Ficoll 70, 15 mg enzyme protein and 18 mg Tris buffer.

EXAMPLE 2

Determination of D-malate in Pure Solutions

The D-malic enzyme converts D-malate to pyruvate and $CO_2$ in the presence of $NAD^+$, during which NDH is formed from $NAD^+$. The NADH concentration is proportional to the concentration of reacted D-malate and can be measured photometrically (absorbance at 339 nm). The measurement can also be carried out with a Hg lamp at 365 nm or 334 nm. The light path of the cuvette is 1 cm, the measurement temperature is 20° to 25° C. and the test volume in the cuvette is 3.01 ml.

Determination of D-malic Acid

Wavelength: 339 nm, Hg 365 nm or Hg 334 nm
Light path: 1 cm
Temperature: 20° to 25° C.
Test volume: 3.01 ml

| Pipette into cuvettes | Blank | Sample | Concentration in the test |
| --- | --- | --- | --- |
| HEPES buffer, pH 9.0 | 1.00 ml | 1.00 ml | 0.05 mol/l |
| $MgCl_2.6H_2O$ | 0.10 ml | 0.10 ml | 3.27 mmol/l |
| NAD | 0.10 ml | 0.10 ml | 0.60 mmol/l |
| redistilled water | 1.80 ml | 1.70 ml | |
| sample or standard solution (D-malate) | — | 0.10 ml | up to ca. 130 μmol/l |
| mix and measure $A_1$ after ca. 5 minutes. Start reaction by the addition of | | | |
| D-MDH | 0.01 ml | 0.01 ml | 265 U/l |
| mix and after the reaction is completed (ca. 20 minutes) measure $A_2$. | | | |

The absorbance ΔA is calculated as follows:
$$\Delta A = (A_2 - A_1)_{sample} - (A_2 - A_1)_{blank}$$

The concentration of D-malate is derived as follows:
$$c = \frac{3.01 \cdot 134.09}{\epsilon \cdot 1 \cdot 0.1 \cdot 1000} \Delta A = [\text{g D-malic acid/l sample solution}]$$

In this equation ε denotes the absorption coefficient of NADH at:
339 nm = 6.3 (l/mmol · cm)
Hg 365 nm = 3.4 (l/mmol · cm)
Hg 334 nm = 6.18 (l/mmol · cm).

EXAMPLE 3

Determination of the D-malate Content in White Wine 10 ml of a wine sample were adjusted to pH 7.0 with KOH (5 mol/l) and filled up to 20 ml with water. The contents are mixed well and subsequently filtered through a folded filter. 1 ml of clear filtrate is used for the test (see Example 2).

We claim:

1. $NAD^+$-dependent D-malate dehydrogenase (decarboxylating, E.C. 1.1.1.83) which is obtainable from *E. coli* DSM 5496, wherein the presence of $K^+$, $Rb^+$ or $NH_4^+$ ions is not necessary for the enzyme activity.

2. Enzyme as claimed in claim 1, wherein its activity is not inhibited by EDTA (0.7 mg/ml test solution).

3. Enzyme as claimed in claim 1 or 2, wherein the conversion of D-malate to pyruvate and $CO_2$ in the presence of $NADP^+$ is less than 0.5% of the conversion in the presence of $NAD^+$.

4. Enzyme as claimed in claim 1 or 2, wherein it consists of two subunits which each have a molecular weight of 42 kD (SDS gel).

5. Enzyme as claimed in claim 1 or 2, wherein it has a specific activity of at least 25 U/mg protein after purification.

6. Reagent for the determination of D-malate, wherein it contains D-malate dehydrogenase as claimed in claim 1, buffer, $Mg^{2+}$ ions and $NAD^+$.

7. Reagent as claimed in claim 6, wherein it contains Tris or/and HEPES buffer.

8. Reagent as claimed in claim 6, wherein it contains 20 mmol/l to 200 mmol/l Tris or/and HEPES buffer, pH 7.5 to 10, 0.6 mmol/l to 10 mmol/l $Mg^{2+}$ ions and 0.3 mmol/l to 5.0 mmol/l $NAD^+$.

9. Reagent as claimed in claim 6, wherein it contains 50 mml/l Tris or/and HEPES buffer, 3.3 mmol/l $Mg^{2+}$ ions and 0.6 mmol/l $NAD^+$.

* * * * *